(12) United States Patent
De Sapio et al.

(10) Patent No.: US 10,676,083 B1
(45) Date of Patent: Jun. 9, 2020

(54) SYSTEM AND METHOD FOR PREDICTION OF OCCUPANT MOTOR RESPONSE IN ACCIDENTS

(71) Applicant: HRL Laboratories, LLC, Malibu, CA (US)

(72) Inventors: Vincent De Sapio, Westlake Village, CA (US); Jaehoon Choe, Agoura Hills, CA (US); Matthew E. Phillips, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 108 days.

(21) Appl. No.: 15/584,905

(22) Filed: May 2, 2017

Related U.S. Application Data

(63) Continuation-in-part of application No. 14/539,898, filed on Nov. 12, 2014.

(60) Provisional application No. 62/330,379, filed on May 2, 2016, provisional application No. 61/903,526, filed on Nov. 13, 2013.

(51) Int. Cl.
*A61F 2/78* (2006.01)
*B60W 30/09* (2012.01)
*A61B 5/18* (2006.01)
*A61B 5/16* (2006.01)

(52) U.S. Cl.
CPC ............ *B60W 30/09* (2013.01); *A61B 5/162* (2013.01); *A61B 5/18* (2013.01)

(58) Field of Classification Search
CPC .......... B60W 30/09; A61B 5/18; A61B 5/162
See application file for complete search history.

(56) References Cited

U.S. PATENT DOCUMENTS

| 5,340,059 A * | 8/1994 | Kanigowski | B64D 25/00 244/118.5 |
| 2011/0130111 A1* | 6/2011 | Crandall | B60R 21/013 455/404.1 |

(Continued)

OTHER PUBLICATIONS

Mitsuhiro Hayashibe et al. "EMG-Based Neuromuscular Modeling with Full Physiological Dynamics and Its Comparison with Modified Hill Model" (Year: 2009).*

(Continued)

*Primary Examiner* — Brian W Wathen
*Assistant Examiner* — Abdou K Seye
(74) *Attorney, Agent, or Firm* — Tope-McKay & Associates

(57) ABSTRACT

Described is a system for prediction and active compensation of occupant motor response in a vehicle accident. The system uses a spinal reflex model to generate a stimulus based on an accident scenario of an occupant in a vehicle, the stimulus being a set of proprioceptive signals induced by the accident scenario. A neuromuscular model then determines activation and contraction dynamics based on the stimulus. The activation and contraction dynamics represent muscle contraction forces spanning a skeletal system of the occupant. A musculoskeletal model then generates a predicted motor response of the occupant based on the activation and contraction dynamics. The predicted motor response can be used for a variety of purposes, such as initiating active compensation in a vehicle or modifying airline cabin design parameters to decrease the likelihood of injury to the occupant.

21 Claims, 6 Drawing Sheets

(56) References Cited

U.S. PATENT DOCUMENTS

| | | | |
|---|---|---|---|
| 2012/0050026 A1* | 3/2012 | Westerblad | B60R 21/0134 340/436 |
| 2013/0310979 A1* | 11/2013 | Herr | B62D 57/032 700/258 |

OTHER PUBLICATIONS

Stepen Dorgan "Amodel for Electrically Activated Mammalian Muscle capturing N-Let Behaviours" (Year: 1996).*

Antona, J., Ejima, S., & Zama, Y. (2011). Influence of the driver conditions on the injury outcome in front impact collisions. International Journal of Automotive Engineering, 2(2), pp. 33-38.

Avela, J., Kyröläinen, H., & Komi, P. V. (1999). Altered reflex sensitivity after repeated and prolonged passive muscle stretching. Journal of Applied Physiology, 86(4), pp. 1283-1291.

Bose, D., Crandall, J. R., Untaroiu, C. D., & Maslen, E. H. (2010). Influence of pre-collision occupant parameters on injury outcome in a frontal collision. Accident Analysis & Prevention, 42(4), pp. 1398-1407.

Brolin, K., Halldin, P., & Leijonhufvud, I. (2005). The effect of muscle activation on neck response. Traffic injury prevention, 6(1), pp. 67-76.

Brolin, K., Gras, L. L., & Stockman, I. (2014). Active spine modeling representing a 6 year-old child. In 7th World Congress of Biomechanics (No. 16-14).

Burke, J. R., Schutten, M. C., Koceja, D. M., & Kamen, G. (1996). Age-dependent effects of muscle vibration and the Jendrassik maneuver on the patellar tendon reflex response. Archives of physical medicine and rehabilitation, 77(6), pp. 600-604.

Ejima, S., Zama, Y., Ono, K., Kaneoka, K., Shiina, I., & Asada, H. (Jun. 2009). Prediction of pre-impact occupant kinematic behavior based on the muscle activity during frontal collision. In 21st ESV Conference (No. 09-0913), pp. 1-11.

Frijns, C. J. M., Laman, D. M., Van Duijn, M. A. J., & Van Duijn, H. (1997). Normal values of patellar and ankle tendon reflex latencies. Clinical neurology and neurosurgery, 99(1), pp. 31-36.

Hayes, K. C. (1975). Effects of fatiguing isometric exercise upon achilles tendon reflex and plantar flexion reaction time components in man. European journal of applied physiology and occupational physiology, 34(1), pp. 69-79.

Ito, D., Ejima, S., Sukegawa, Y., Antona, J., Ito, H., & Komeno, F. (2013). Assessment of a pre-crash seatbelt technology in frontal impacts by using a new crash test sled system with controllable pre-impact braking. In 23rd international technical conference on the enhanced safety of vehicles, pp. 1-9.

Iwamoto, M., Nakahira, Y., & Sugiyama, T. (2011). Investigation of pre-impact bracing effects for injury outcome using an active human FE model with 3D geometry of muscles. In 22nd International Technical Conference on the Enhanced Safety Vehicles, Paper No. 11-0150, pp. 1-15.

Kirschbichler, S., Sinz, W., Prüggler, A., Huber, P., & Steiner, K. (2011). Detailed analysis of 3d occupant kinematics and muscle activity during the pre-crash phase as basis for human modeling based on sled tests. In 22th International Technical Conference on the Enhanced Safety of Vehicles (ESV), Washington, USA, Paper (No. 11-0162), pp. 1-8.

Östh, J., Brolin, K., Ólafsdóttir, J. M., Davidsson, J., Pipkorn, B., Jakobsson, L., Törnvall, F. & Lindkvist, M. (2015). Muscle Activation Strategies in Human Body Models for the Development of Integrated Safety. In 24th International Technical Conference on the Enhanced Safety of Vehicles (ESV) (No. 15-0345), pp. 1-15.

Stam, J., & Tan, K. M. (1987). Tendon reflex variability and method of stimulation. Electroencephalography and clinical neurophysiology, 67(5), pp. 463-467.

Stemper, B. D., Yoganandan, N., Pintar, F. A., & Rao, R. D. (2006). Anterior longitudinal ligament injuries in whiplash may lead to cervical instability. Medical engineering & physics, 28(6), pp. 515-524.

Toyota, Total Human Model for Safety (THUMS) virtual human model software, Toyota Global Newsroom, Jun. 26, 2105, pp. 1-2.

Zhang, L. Q., Huang, H., Sliwa, J., & Rymer, W. Z. (1999). System identification of tendon reflex dynamics. Rehabilitation Engineering, IEEE Transactions on, 7(2), pp. 193-203.

Anderson, F.C. and Pandy, M.G. (2001) 'Dynamic optimization of human walking', Journal of Biomechanical Engineering, vol. 123, No. 5, pp. 381-390.

Anderson, F.C. and Pandy, M.G. (2001) 'Static and dynamic optimization solutions for gait are practically equivalent', Journal of Biomechanics, vol. 34, No. 2, pp. 153-161.

Crowninshield, R.D. and Brand, R.A. (1981) 'A physiologically based criterion of muscle force prediction in locomotion', Journal of Biomechanics, vol. 14, No. 11, pp. 793-801.

Davy, D.T. and Audu, M.L. (1987) 'A dynamic optimization technique for predicting muscle forces in the swing phase of gait', Journal of Biomechanics, vol. 20, No. 2, pp. 187-201.

De Sapio, V. (2011) 'Task-level control of motion and constraint forces in holonomically constrained robotic systems', in Proceedings of the 18th World Congress of the International Federation of Automatic Control, pp. 14622-14629.

De Sapio, V. and Park, J. (2010) 'Multitask constrained motion control using a mass-weighted orthogonal decomposition', Journal of Applied Mechanics, vol. 77, No. 4, pp. 041004-1 through 041004-10.

De Sapio, V., Khatib, O., and Delp, S. (2006) 'Task-level approaches for the control of constrained multibody systems', Multibody System Dynamics, vol. 16, No. 1, pp. 73-102.

De Sapio, V., Khatib, O. and Delp, S. (2005) 'Simulating the task-level control of human motion: a methodology and framework for implementation', The Visual Computer, vol. 21, No. 5, pp. 289-302.

Kaplan, M.L. and Heegaard, J.H. (2001) 'Predictive algorithms for neuromuscular control of human locomotion', Journal of Biomechanics, vol. 34, No. 8, pp. 1077-1083.

Khatib, O. (1995) 'Inertial properties in robotic manipulation: an object level framework', International Journal of Robotics Research, vol. 14, No. 1, pp. 19-36.

Khatib, O., Sentis, L., Park, J., and Warren, J. (2004) 'Whole-body dynamic behavior and control of human-like robots', International Journal of Humanoid Robotics, vol. 1, No. 1, pp. 29-43.

Siciliano, B., & Khatib, O. (Eds.). (2008). Chapter 6, Section 6.6, pp. 143-146, Springer Handbook of Robotics. Springer.

Neptune, R.R. (1999) 'Optimization algorithm performance in determining optimal controls in human movement analyses', Journal of Biomechanical Engineering, vol. 121, No. 2, pp. 249-252.

Sentis, L., Park, J. and Khatib, O. (2010) 'Compliant control of multicontact and center-of-mass behaviors in humanoid robots', IEEE Transactions on Robotics, vol. 26, No. 3, pp. 483-501.

Thelen, D.G. and Anderson, F.C. (2006) 'Using computed muscle control to generate forward dynamic simulations of human walking from experimental data', Journal of Biomechanics, vol. 39, No. 6, pp. 1107-1115.

Thelen, D.G., Anderson, F.C. and Delp, S.L. (2003) 'Generating dynamic simulations of movement using computed muscle control', Journal of Biomechanics, vol. 36, No. 3, pp. 321-328.

Office Action 1 for U.S. Appl. No. 14/539,898, dated Sep. 8, 2017.

Response to Office Action 1 for U.S. Appl. No. 14/539,898, dated Feb. 7, 2018.

Carlos Rengifo et al. "Optimal control of a neuromusculoskeletal model: a second order sliding mode solution", 2008 IEEE, pp. 55-60.

Fady Alnajjar et al. "A bio-inspired neuromuscular model to simulate the neuro-sensorimotor basis for postural-reflex-response in Humans", The Fourth IEEE RAS/EMBS International Conference on Biomedical Robotics and Biomechatronics Roma, Italy. Jun. 24-27, 2012, p. 980-985.

Office Action 2 for U.S. Appl. No. 14/539,898, dated May 31, 2018.

Vincent De Sapio, et al., "Task-level approaches for the control of constrained multibody systems," 2006.

Response to Office Action 2 for U.S. Appl. No. 14/539,898, dated Oct. 1, 2018.

(56) References Cited

OTHER PUBLICATIONS

Lewis, F.L., Abdallah, C.T. and Dawson, D.M. (1993) in "Control of Robot Manipulators", Macmillan Publishing Company, New York, Chapter 4, pp. 169-260.

* cited by examiner

SYSTEM AND METHOD FOR PREDICTION OF OCCUPANT MOTOR RESPONSE IN ACCIDENTS

CROSS-REFERENCE TO RELATED APPLICATIONS

This is a Continuation-in-Part application of U.S. application Ser. No. 14/539,898, filed on Nov. 12, 2014, which is a non-provisional application of U.S. Provisional Application No. 61/903,526, filed on Nov. 13, 2013, the entirety of which are hereby incorporated by reference.

This application is ALSO a non-provisional patent application of U.S. Provisional Application No. 62/330,379, filed on May 2, 2016, the entirety of which is hereby incorporated by reference.

BACKGROUND OF INVENTION

(1) Field of Invention

The present invention relates to a vehicle safety system and, more specifically, to a vehicle safety system that provides for real-time prediction and active compensation based on occupant response in an accident.

(2) Description of Related Art

Occupant muscle and motor response in the event of an automobile accident can lead to a variety of injuries. Current state of the art vehicle and airline accident simulations model only passive structural elements of the human body to elucidate potential injury mechanisms and fail to consider active motor responses. As noted by several researchers, these kinematics significantly influence injury outcome (see Literature Reference Nos, 1, 3, 10, 11, and 12). Occupants typically brace themselves just before an accident and roughly half of drivers take defensive action, such as sudden braking or steering, to avoid collisions. Passive computational models and anthropomorphic test devices (ATDs) are not able to model such defensive actions. Additionally, autonomous vehicles may maneuver in evasive/emergency contexts that do not take passenger injury potential into account.

As a result, it is desirable to understand various muscle states and actions before and after such a collision to provide for active compensation to minimize injuries. Nevertheless, limited prior art exists related to active motor control models to predict occupant posture and injury outcome. Toyota, for example, is currently working on a system incorporated into their Total Human Model for Safety (THUMS) virtual human model software that attempts to model muscle activity prior to collisions (see the List of Incorporated Literature References, Literature Reference No. 16).

In other prior art, Ejinma, et al., conducted low speed frontal impact tests on human subjects using a sled-mounted rigid seat, on which each subject sat (see Literature Reference No. 7). Electromyography (EMG) electrodes were attached to the skin over the major muscles of each subject to examine the effect of muscle activity on the physical motion in the pre-crash event. It was found that head-neck-torso kinematics was strongly influenced by muscle activity. Additionally, the authors conducted a simulation study using the commercial software, MADYMO™, with a multibody adult male as the occupant model. Muscles were modeled using a Hill-type muscles. Validation of the model against the experimental EMG data was performed.

In other art, cervical spine models have been investigated (see Literature Reference Nos. 4, 13, and 15). However, while these models address the structure of the neck and the activity of muscles spanning the neck, they do not model reflex circuits in the spinal cord, which can be used to determine reflexive motor behavior in pre-crash situations.

While the prior art provided limited research in predicting occupant posture and injury outcome, the prior art failed in providing a complete solution to reduce injuries. Thus, a continuing need exists for a system that provides for real-time prediction and active compensation based on occupant response in an accident.

SUMMARY OF INVENTION

This disclosure provides a system for prediction and active compensation of occupant motor response in a vehicle accident. The system includes one or more processors and a memory. The memory is a non-transitory computer-readable medium having executable instructions encoded thereon, such that upon execution of the instructions, the one or more processors perform several operations. For example, the system uses a spinal reflex model to generate a stimulus based on an accident scenario of an occupant in a vehicle, the stimulus being a set of proprioceptive signals induced by the accident scenario. A neuromuscular model then determines activation and contraction dynamics based on the stimulus. The activation and contraction dynamics represent muscle contraction forces spanning a skeletal system of the occupant. A musculoskeletal model then generates a predicted motor response of the occupant based on the activation and contraction dynamics.

In another aspect, the system performs an operation of transmitting proprioceptive signals from the neuromuscular and musculoskeletal models back to the spinal reflex model.

In yet another aspect, the accident scenario includes one or more parameters indicative of a physical impact to a vehicle having an occupant therein.

Further, the spinal reflex model is a functional model of a human spinal cord that models spinal circuits influencing reflexive motor outputs.

In another aspect, the system is incorporated into a vehicle as an active vehicle compensation system, such that based on a predicted outcome given a specified occupant and vehicle model, the system initiates active compensation of the vehicle. The active compensation includes, for example, adjusting one or more parameters within the vehicle.

In yet another aspect, the system performs an operation of generating a predicted injury to the occupant based on the accident scenario and the vehicle.

In another aspect, the system is incorporated into an airline cabin safety design system, such that based on the predicted injury, the system adjusts airline cabin design parameters until the predicted injury is below a predetermined threshold.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
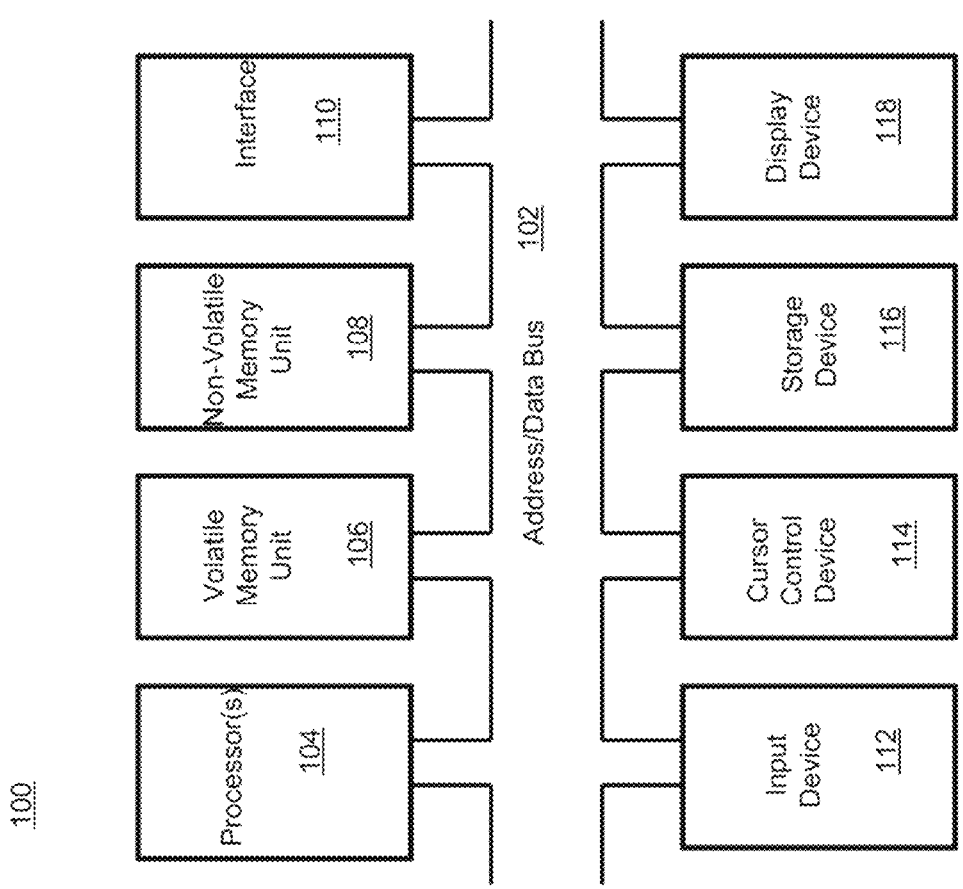
FIG. 1 is a block diagram depicting the components of a system according to various embodiments of the present invention.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of incorporated literature references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) LIST OF INCORPORATED LITERATURE REFERENCES

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Antona, J., Ejima, S., & Zama, Y. (2011). Influence of the driver conditions on the injury outcome in front impact collisions. *International Journal of Automotive Engineering*, 2(2).
2. Avela, J., Kyröläinen, H., & Komi, P. V. (1999). Altered reflex sensitivity after repeated and prolonged passive muscle stretching. *Journal of Applied Physiology*, 86(4), 1283-1291.
3. Bose, D., Crandall, J. R., Untaroiu, C. D., & Maslen, E. H. (2010). Influence of pre-collision occupant parameters on injury outcome in a frontal collision. *Accident Analysis & Prevention*, 42(4), 1398-1407.
4. Brolin, K., Halldin, P., & Leijonhufvud, I. (2005). The effect of muscle activation on neck response. *Traffic injury prevention*, 6(1), 67-76.
5. Brolin, K., Gras, L. L., & Stockman, I. (2014). Active spine modeling representing a 6 year-old child. In 7*th World Congress of Biomechanics* (No. 16-14).
6. Burke, J. R., Schutten, M. C., Koceja, D. M., & Kamen, G. (1996). Age-dependent effects of muscle vibration and the Jendrassik maneuver on the patellar tendon reflex response. *Archives of physical medicine and rehabilitation*, 77(6), 600-604.
7. Ejima, S., Zama, Y., Ono, K., Kaneoka, K., Shiina, I., & Asada, H. (2009, June). Prediction of pre-impact occupant kinematic behavior based on the muscle activity during frontal collision. In 21*st ESV Conference* (No. 09-0913).
8. Frijns, C. J. M., Laman, D. M., Van Duijn, M. A. J., & Van Duijn, H. (1997). Normal values of patellar and ankle tendon reflex latencies. *Clinical neurology and neurosurgery*, 99(1), 31-36.
9. Hayes, K. C. (1975). Effects of fatiguing isometric exercise upon achilles tendon reflex and plantar flexion reaction time components in man. *European journal of applied physiology and occupational physiology*, 34(1), 69-79.
10. Ito, D., Ejima, S., Sukegawa, Y., Antona, J., Ito, H., & Komeno, F. (2013). Assessment of a pre-crash seatbelt technology in frontal impacts by using a new crash test sled system with controllable pre-impact braking. In 23*rd international technical conference on the enhanced safety of vehicles*.
11. Iwamoto, M., Nakahira, Y., & Sugiyama, T. (2011). Investigation of pre-impact bracing effects for injury outcome using an active human FE model with 3D geometry of muscles. In 22*nd International Technical Conference on the Enhanced Safety Vehicles* (pp. 11-0150).
12. Kirschbichler, S., Sinz, W., Prüggler, A., Huber, P., & Steiner, K. (2011). Detailed analysis of 3d occupant kinematics and muscle activity during the pre-crash phase as basis for human modeling based on sled tests. In 22*th*

International Technical Conference on the Enhanced Safety of Vehicles (ESV), Washington, USA, Paper (No. 11-0162).
13. Östh, J., Brolin, K., Ólafsdóttir, J. M., Davidsson, J., Pipkorn, B., Jakobsson, L., Törnvall, F. & Lindkvist, M. (2015). Muscle Activation Strategies in Human Body Models for the Development of Integrated Safety. In 24th International Technical Conference on the Enhanced Safety of Vehicles (ESV) (No. 15-0345).
14. Stam, J., & Tan, K. M. (1987). Tendon reflex variability and method of stimulation. Electroencephalography and clinical neurophysiology, 67(5), 463-467.
15. Stemper, B. D., Yoganandan, N., Pintar, F. A., & Rao, R. D. (2006). Anterior longitudinal ligament injuries in whiplash may lead to cervical instability. Medical engineering & physics, 28(6), 515-524.
16. Toyota, Total Human Model for Safety (THUMS) virtual human model software, Toyota Global Newsroom, Jun. 26, 2105.
17. Zhang, L. Q., Huang, H., Sliwa, J., & Rymer, W. Z. (1999). System identification of tendon reflex dynamics. Rehabilitation Engineering, IEEE Transactions on, 7(2), 193-203.

(2) PRINCIPAL ASPECTS

Various embodiments of the invention include three "principal" aspects. The first is a system for prediction and active compensation of occupant motor response in accidents. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. Importantly, the system 100 includes any hardware, circuitry, sensors, etc. as may be necessary to perform any of the calculations, processes, operations, and/or functions as described herein. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
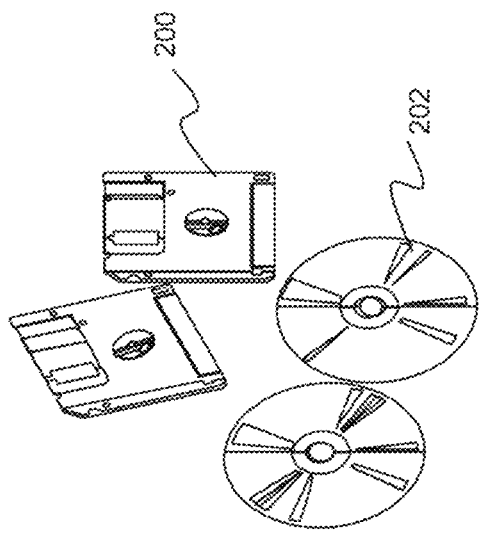
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) INTRODUCTION

This disclosure provides a system-level approach to predict occupant (driver/passenger) motor response in vehicle and airline accident scenarios. Current state of the art vehicle and airline accident simulations model only passive structural elements of the human body to elucidate potential injury mechanisms. The invention of this disclosure takes into account active motor response that is critical in predicting the kinematics of the human body prior to impact.

Rather than just analyze the affect of human posture on crash outcomes, the system of this disclosure uses motor and spinal reflex models to predict motor response which directly influences posture and motor actions like steering and breaking in crash scenarios. Thus, the invention addresses the need to model the active motor response of the human driver/passenger preceding an impending accident or during evasive maneuver. In doing so, the system provides enhanced insight into dynamic driver/passenger motor behaviors that may mitigate (or amplify) injury but cannot be predicted by current simulations.

As can be appreciated by those skilled in the art, there are several applications in which the system described herein can be effectively employed. As a non-limiting example, an application includes improved cabin safety design based on predicted behavior of drivers/passengers. This invention can be used by ergonomists to create improved cabin designs based on spinal reflex and motor models that predict how human occupants respond immediately preceding and during an accident scenario. These models will allow ergonomists to perform targeted design optimizations of cabin features to complement the way in which occupants control their body postures in accident scenarios. The resulting designs will better protect occupants based on predictive knowledge of occupant motor response.

Another application includes real-time active safety system compensation based on state measurements/estimates and predictions of driver control actions (steering, braking, etc.) and driver/passenger postural state. For example, there are a number of active safety systems that can exploit this invention to achieve optimal safety outcomes based on predicted passenger state just before impact. These active safety systems include, for example, active seat adjustment, airbag deployment, etc.

With autonomous driving technologies becoming increasingly important, there are also applications to real-time active safety system compensation for autonomous driving based on state measurements/estimates and predictions of passenger postural state and predictions of actions associated with other drivers.

(4) SPECIFIC DETAILS OF VARIOUS EMBODIMENTS

Figure 3:
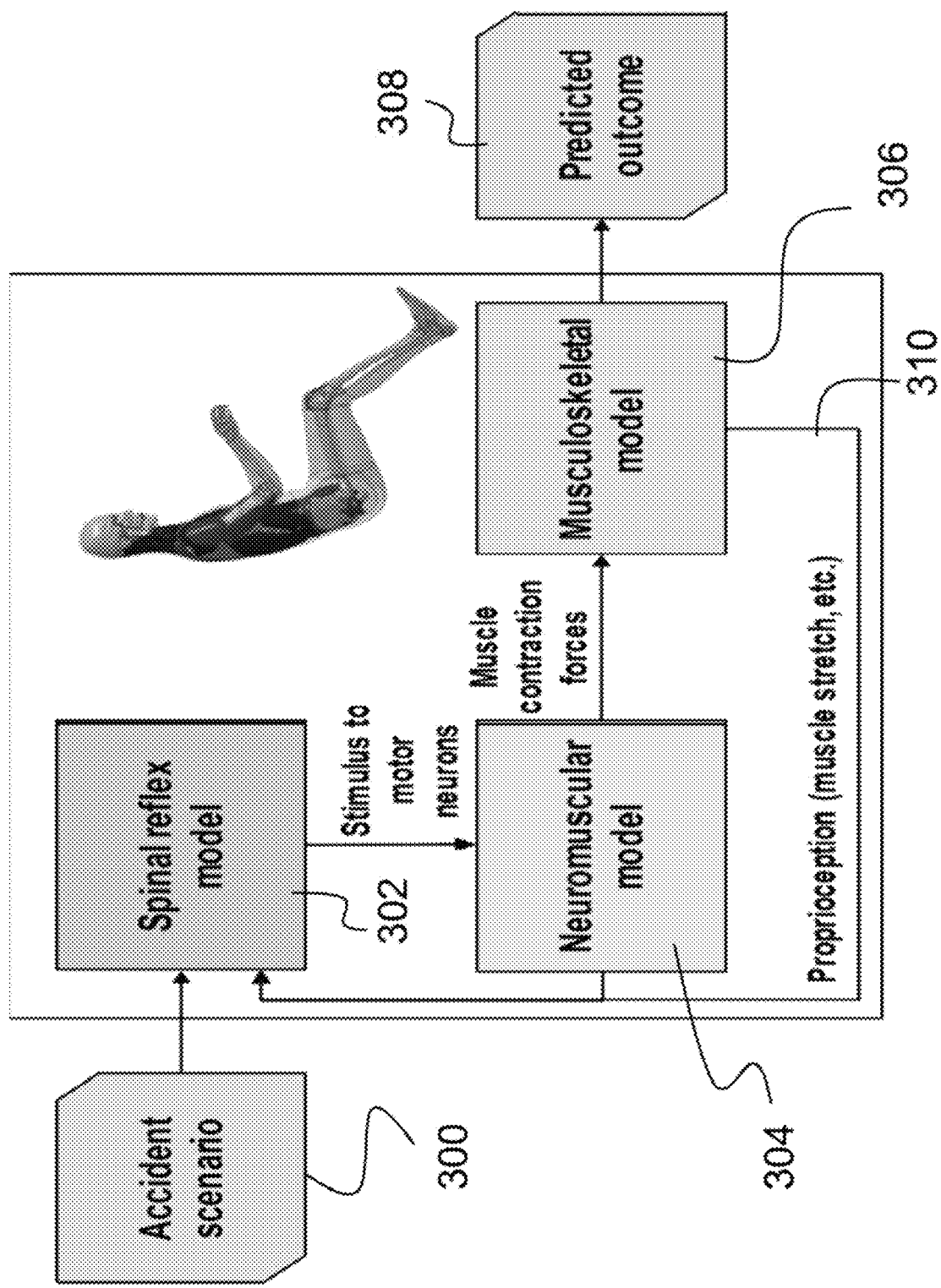
FIG. 3 is an illustration depicting a system level diagram of a predictive motor response component of a system according to various embodiments of the present invention.

As noted above, this disclosure provides a system-level approach to predict occupant (driver/passenger) motor response in vehicle accident scenarios. FIG. 3, for example, illustrates system level architecture of the predictive motor response component of the invention. The accident scenario 300 provides input to a spinal reflex model 302 which outputs stimulus to the neuromuscular model 304. The spinal reflex model 302 is a functional model of the human spinal cord that models spinal circuits influencing reflexive motor outputs. Outputs of the spinal reflex model 32 include neural signaling to individual muscles/muscle groups and estimates for approximate motor unit recruitment and subsequent signal transduction to the neuromuscular model 34M. Inputs back to the spinal reflex model 302 include position and dynamics from muscles to provide muscle stretch data.

For example, the accident scenario 300 is a modelled or real accident in a vehicle that includes parameters indicative of a physical impact to a vehicle having an occupant therein, such as the forces associated with deceleration of a vehicle based upon impact, etc. The input from the accident scenario 300 to the spinal reflex model 302 involves a set of human proprioceptive (sensory function) signals, induced by the accident scenario, that initiates a reflex arc. For example, the physics of the accident scenario (accident kinetics) will stimulate somatic receptors, like tendon sense organs and muscle stretch receptors. Based on afferent signals from these modelled somatic receptors, the spinal reflex model 302 then outputs efferent stimulus, such as the neural signaling to the muscles, etc, to complete the reflex arc.

After receiving the stimulus, the neuromuscular model 304 determines the activation and contraction dynamics (i.e., muscle contraction forces) of the muscles spanning the skeletal system. The motor response (i.e., predicted outcome 308) of the occupant is computed by the musculoskeletal model 306 from the output of the neuromuscular model 304. Proprioceptive signals 310 from the neuromuscular and musculoskeletal models are then fed back to the spinal reflex model 302.

The spinal reflexes (i.e., the stimulus to the neuromuscular model 304) by the spinal reflex model 302 are modeled from biological units, but simplified to three primary components—spinal cord circuits, tendon sense organs, and afferent/efferent pathways that form the sensory/motor loop. Through integration of physiological data from in vivo human studies, parameters for tendon reflex activity and thresholds for muscle activation can be built to enable prediction of reflex-based muscle activation in a variety of scenarios. Non-limiting examples of such scenarios include likelihood of motor pool recruitment (see Literature Reference No. 6), muscle specificity (see Literature Reference Nos. 14 and 17), and reflex timing (see Literature Reference No. 8). Additionally, effects of muscle stretch, repeated activations, and fatigue can also be integrated into the model to shape predicted motor unit recruitment (see Literature Reference No. 2). By identifying functions that can compute these probabilities across all potential positions and forces involved within vehicular crash scenarios, the neurophysiological model can then be discretized and instantiated in multi-body models efficiently.

The neuromuscular dynamics are modeled by the neuromuscular model 304 using a Hill-type active state model. The states include the r muscle activations, a, and the muscle fiber lengths, $l_M$. The state derivatives can be expressed functionally as, $$\dot{a} = \dot{a}(a,u), \text{and,}$$

$$\dot{l}_M = \dot{l}_M(q, \dot{q}, a, l_M),$$

where u is the muscle excitation (control input to the plant). The musculo-tendon force is given as, $$f_T = f_T(q, l_M).$$

The relationship between muscle force and joint torque is given by, $$\tau = R(q)f_T,$$

where R is the matrix of muscle moment arms, q is the vector of n generalized or joint coordinates, and $\tau$ is the vector of applied joint torques (derived from muscle forces acting over the joints). Expressed in state space form the musculoskeletal dynamics are, $$\dot{v} = M(q)^{-1}[R(q)f_T(q,l_M) - b(q,v) - g(q) - f_{ext}], \text{and,}$$

$$\dot{q} = v.$$

where M(q), is the joint space mass matrix, $b(q,\dot{q})$, is the vector of centrifugal and Coriolis forces, g(q) is the vector of gravity forces, and $f_{ext}$ are external forces acting on the biomechanical system. The 2n+2r first order state equations for the entire neuromechanical plant are then, $$\begin{pmatrix} \dot{a} \\ \dot{l}_M \\ \dot{q} \\ \dot{v} \end{pmatrix} = F(a, l_M, q, v, u, f_{ext}).$$

Figure 4:
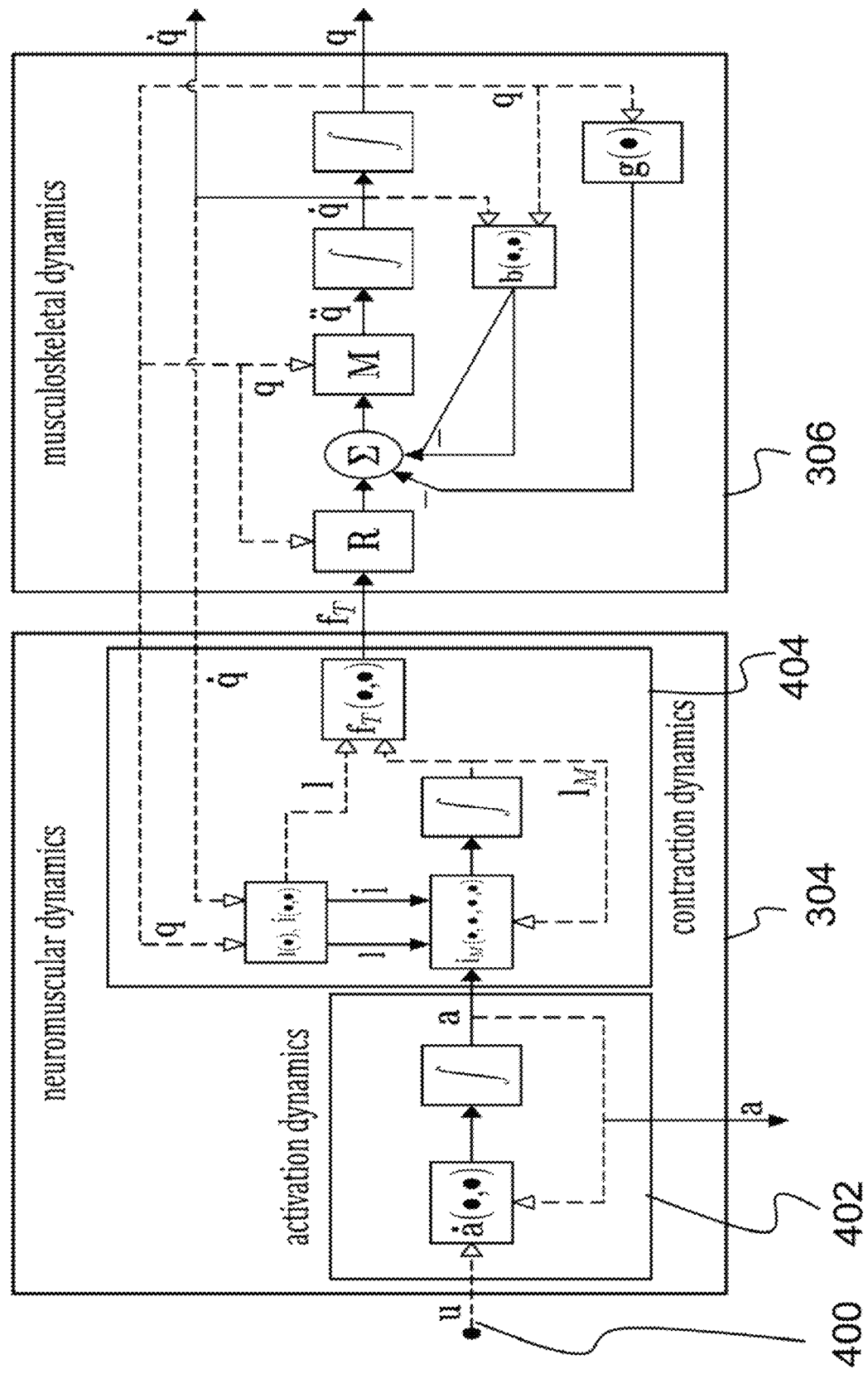
FIG. 4 is an illustration depicting a neuromuscular and musculoskeletal system (feed-forward path)

The neuromuscular and musculoskeletal dynamics can be represented as shown in FIG. 4, which depicts a feed-forward path for the neuromuscular and musculoskeletal models 304 and 306. The models are physics-based neuromuscular and musculoskeletal simulation environment with the ability to compute muscle activation and contraction dynamics based on input neural excitations to individual muscles.

Neural inputs 400 from the spinal reflex model trigger the muscle activation dynamics 402. Output of the activation dynamics 402 provides input to the contraction dynamics 404. Output of the contraction dynamics 404 provides input to the musculoskeletal model 306 through the tendon forces. The musculoskeletal model 306 then generates a predicted outcome involving bodily motion, such as flexion/extension of specific joints, associated with the contraction of specific muscles. Further, proprioceptive signals from the neuromuscular and musculoskeletal models 304 and 306 are then fed back to the spinal reflex model.

Further details regarding the neuromuscular and musculoskeletal models 304 and 306 can be found at U.S. non-provisional application Ser. No. 14/539,898, which is incorporated by reference as though fully set forth herein.

Figure 5:
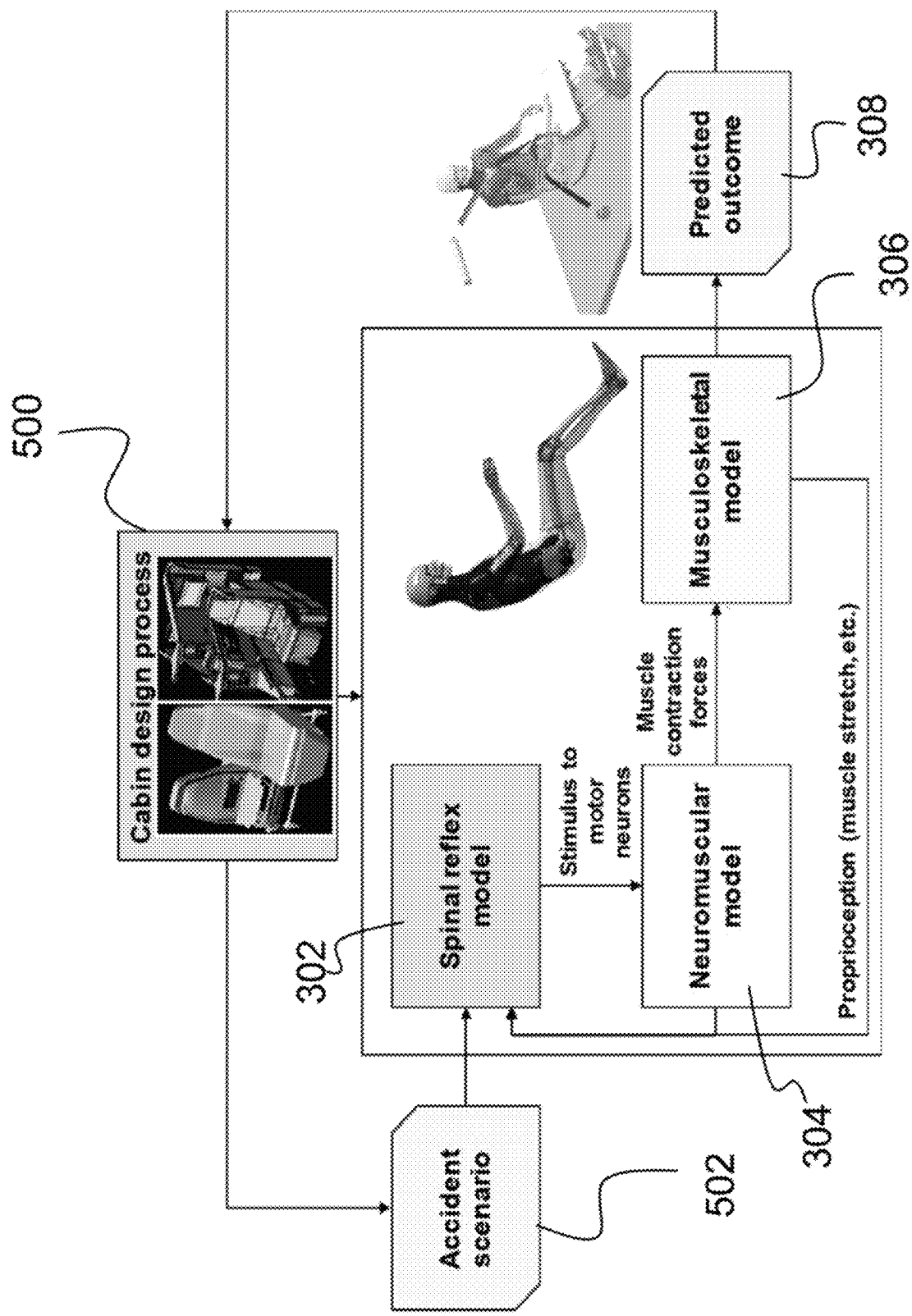
FIG. 5 is an illustration depicting a system level architecture for airline cabin safety design and analysis based on predicted motor response of passengers.

As noted above, the system as described herein has several applications. As a non-limiting example, FIG. 5 provides a system level architecture for a use case involving airline cabin safety design and analysis based on predicted motor response of passengers. First, physical design for cabin seats and safety features is specified 500. An accident scenario 502 is also specified (e.g. emergency landing, etc.). The spinal reflex 302, neuromuscular 304, and musculoskeletal 306 models collectively predict the occupant motor response. A computational physics simulation then computes the predicted injury outcome 308 of the occupant. This is fed back to the cabin designers who iterate on the design until an acceptable outcome for the scenario is achieved. For example, the system may automatically adjust design parameters, such as seat width, spacing between seats, etc. until the predicted injury outcome 308 is below a predetermined threshold, such as no injury.

Figure 6:
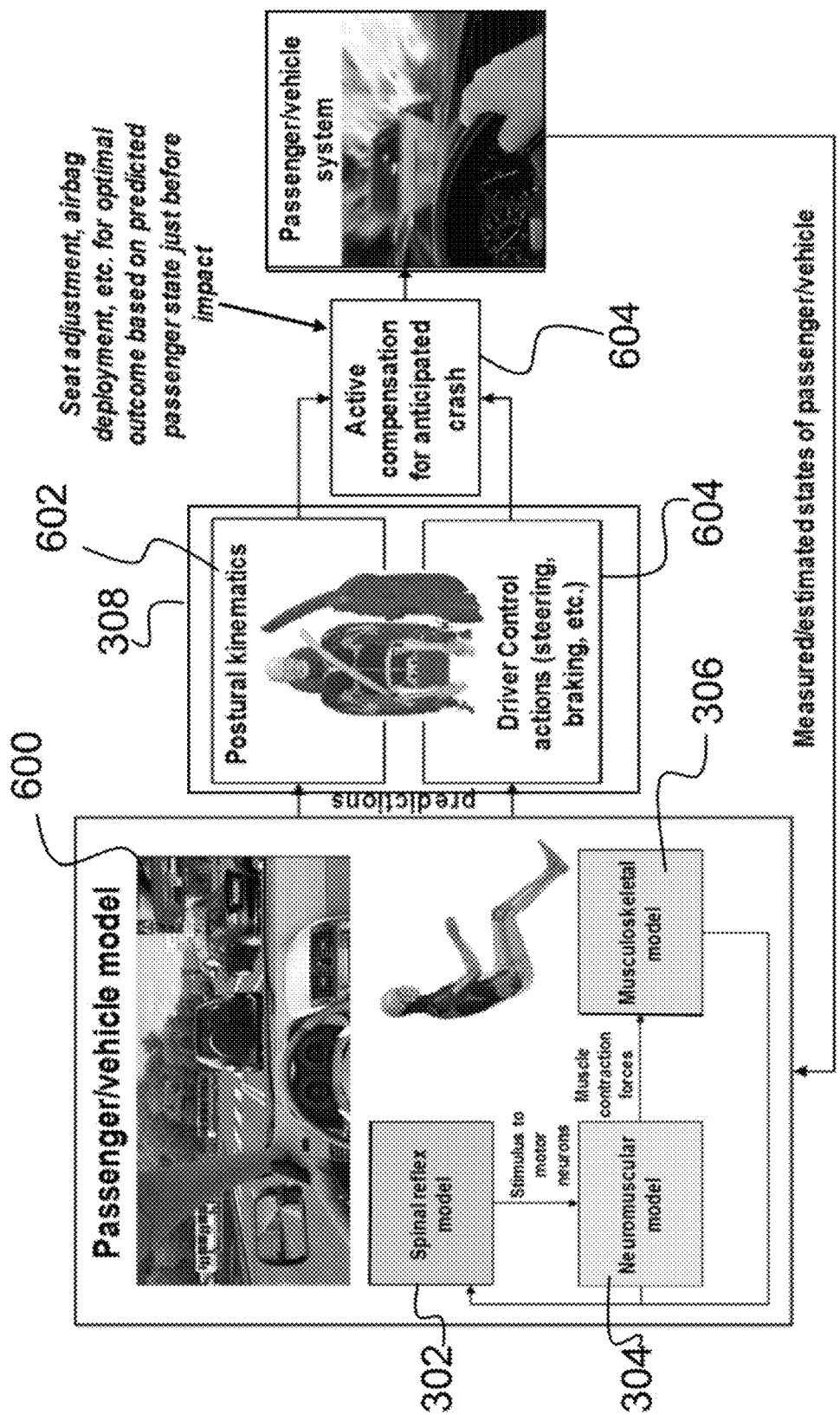
FIG. 6 is an illustration depicting a system level architecture for real-time active safety system compensation based on state measurements/estimates and predictions of driver control actions (steering, braking, etc.) and driver/passenger postural state.

Another non-limiting example application is depicted in FIG. 6. FIG. 6 depicts a system level architecture for a case involving real-time active safety system compensation based on state measurements/estimates and predictions of driver control actions (steering, braking, etc.) and driver/passenger postural state. During operation, a passenger/vehicle model 600 is first specified. This represents the coupled physics of the vehicle and biomechanics of the driver/passenger. Measured/estimated states of the passenger/vehicle are fed to this model. Examples of such measured/estimated states of the passenger/vehicle include vehicle inertial quantities like translational and angular velocity, steering rate, as well as the passengers' postural configurations, etc. The spinal reflex 302, neuromuscular 304, and musculoskeletal 306 models then collectively predict the occupant motor response 308. The predicted motor response 308 includes, for example, muscle, body, and limb movement and/or position. This results in a predicted change to the postural kinematics 602 of the driver/passenger as well as a predicted set of control actions 604 (e.g. steering, braking). Based on these predictions, active compensation 606 is engaged, such as adjusting seat configuration or parameters associated with airbag deployment, braking, steering, etc., in anticipation of a crash. For example, such a vehicle may include sensors that can measure the configuration of the seats and occupants. The vehicle would also include a feedback loop from the vehicle sensors to the vehicle/passenger models incorporating compensation from vehicle active safety systems based on the predicted passenger motor response. For example, if the system predicts that the passenger will contort to a posture that will increase the severity of injury, then the system may cause the vehicle to adjust the seat configuration prior to impact to mitigate the degree of injury to the passenger.

In various aspects the system also includes a physics-based vehicle driving simulation (e.g. CarSim™, Adams Car™) that couples to neuromuscular and musculoskeletal models (e.g., running in simulations like OpenSim). This coupled simulation is used to predict vehicle dynamics and the affect on the passenger body dynamics.

In other aspects, the system also includes a physics-based crash test simulation environment (e.g., MADYMO™, LS-DYNA™ running Global Human Body Modelling Consortium models) that uses multibody and/or finite element solvers to compute quantitative crash outcomes for the vehicle and human occupant. Occupant kinematics and active muscle forces are determined using neuromuscular and musculoskeletal models. From this, the simulation environment then predicts the injury to the occupant (tissue, organs, etc.) due to the crash conditions.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for prediction of occupant motor response in a vehicle accident, the system comprising:
    one or more processors and a memory, the memory being a non-transitory computer-readable medium having executable instructions encoded thereon, such that upon execution of the instructions, the one or more processors perform operations of:
    using a spinal reflex model, generating a stimulus based on an accident scenario of an occupant in a vehicle, the stimulus being a set of proprioceptive signals induced by the accident scenario;
    using a neuromuscular model, determining activation and contraction dynamics based on the stimulus, the activation and contraction dynamics representing muscle contraction forces spanning a skeletal system of the occupant;
    using a musculoskeletal model, generating, a predicted motor response of the occupant based on the activation and contraction dynamics, the predicted motor response includes a predicted change to postural kinematics of the occupant and a predicted set of driver control actions; and
    causing a vehicle, based on a predicted outcome given a specified occupant and vehicle model, to initiate active compensation of the vehicle and, in doing so, causing the vehicle to perform an actual physical operation to mitigate a degree of injury to the occupant, and
    wherein the neuromuscular model uses a Hill-type active state model, where states include r muscle activations, a, and muscle fiber lengths, $l_M$. The state derivatives can be expressed functionally as, $\dot{a}=\dot{a}(a,u)$, and, $\dot{l}_M=\dot{l}_M(q,\dot{q},a,l_M)$, where u is a muscle excitation, and a musculo-tendon force $f_T$ is given as, $f_T=f_T(q,l_M)$, where a relationship between muscle force and joint torque is given by, $\tau=R(q)f_T$, where R is a matrix of muscle moment arms, q is a vector of n generalized or joint coordinates, and $\tau$ is a vector of applied joint torques, and when expressed in state space form, musculoskeletal dynamics are, $\dot{v}=M(q)^{-1}[R(q)f_T(q,l_M)-b(q,v)-g(q)-f_{ext}]$, and, $\dot{q}=v$.

where $M(q)$, is a joint space mass matrix, $b(q,\dot{q})$, is a vector of centrifugal and Coriolis forces, $g(q)$ is a vector of gravity forces, and $f_{ext}$ are external forces acting on the occupant.

2. The system as set forth in claim 1, further comprising an operation of applying proprioceptive signals from the neuromuscular and musculoskeletal models back to the spinal reflex model.

3. The system as set forth in claim 2, wherein the accident scenario includes one or more parameters indicative of a physical impact to a vehicle having an occupant therein.

4. The system as set forth in claim 3, wherein the spinal reflex model is a functional model of a human spinal cord that models spinal circuits influencing reflexive motor outputs.

5. The system as set forth in claim 4, wherein the active compensation includes adjusting a seat configuration of a seat within the vehicle.

6. The system as set forth in claim 4, further comprising an operation of generating a predicted injury to the occupant based on the accident scenario and the vehicle.

7. The system as set forth in claim 6, wherein the system is incorporated into an airline cabin safety design system, such that based on the predicted injury, the system adjusts airline cabin design parameters until the predicted injury is below a predetermined threshold.

8. A computer program product for prediction of occupant motor response in a vehicle accident, the computer program product comprising:
    a non-transitory computer-readable medium having executable instructions encoded thereon, such that upon execution of the instructions by one or more processors, the one or more processors perform operations of:
    using a spinal reflex model, generating a stimulus based on an accident scenario of an occupant in a vehicle, the stimulus being a set of proprioceptive signals induced by the accident scenario;
    using a neuromuscular model, determining activation and contraction dynamics based on the stimulus, the activation and contraction dynamics representing muscle contraction forces spanning a skeletal system of the occupant;

using a musculoskeletal model, generating, a predicted motor response of the occupant based on the activation and contraction dynamics, the predicted motor response includes a predicted change to postural kinematics of the occupant and a predicted set of driver control actions; and causing a vehicle, based on a predicted outcome given a specified occupant and vehicle model, to initiate active compensation of the vehicle and, in doing so, causing the vehicle to perform an actual physical operation to mitigate a degree of injury to the occupant; and wherein the neuromuscular model uses a Hill-type active state model, where states include r muscle activations, a, and muscle fiber lengths, $l_M$, The state derivatives can be expressed functionally as, $\dot{a}=\dot{a}(a,u)$, and, $\dot{l}_M=\dot{l}_M(q,\dot{q},a,l_M)$, where u is a muscle excitation, and a musculo-tendon force $f_T$ is given as, $f_T=f_T(q,l_M)$, where a relationship between muscle force and joint torque is given by, $\tau=R(q)f_T$, where R is a matrix of muscle moment arms, q is a vector of n generalized or joint coordinates, and τ is a vector of applied joint torques, and when expressed in state space form, musculoskeletal dynamics are, $\dot{v}=M(q)^{-1}[R(q)f_T(q,l_M)-b(q,v)-g(q)-f_{ext}]$, and, $\dot{q}=v$, where M(q), is a joint space mass matrix, $b(q,\dot{q})$, is a vector of centrifugal and Coriolis forces, g(q) is a vector of gravity forces, and $f_{ext}$ are external forces acting on the occupant.

9. The computer program product as set forth in claim 8, further comprising an operation of applying proprioceptive signals from the neuromuscular and musculoskeletal models back to the spinal reflex model.

10. The computer program product as set forth in claim 9, wherein the accident scenario includes one or more parameters indicative of a physical impact to a vehicle having an occupant therein.

11. The computer program product as set forth in claim 10, wherein the spinal reflex model is a functional model of a human spinal cord that models spinal circuits influencing reflexive motor outputs.

12. The computer program product as set forth in claim 11, wherein the active compensation includes adjusting a seat configuration of a seat within the vehicle.

13. The computer program product as set forth in claim 11, further instructions for causing on or more processors to perform an operation of generating a predicted injury to the occupant based on the accident scenario and the vehicle.

14. The computer program product as set forth in claim 13, further comprising instructions for causing an airline cabin safety design system, based on the predicted injury, to adjust airline cabin design parameters until the predicted injury is below a predetermined threshold.

15. A method for prediction of occupant motor response in a vehicle accident, the method comprising:

causing one or more processors to execute instructions encoded on a non-transitory computer-readable medium, such that upon execution, the one or more processors perform operations of:

using a spinal reflex model, generating a stimulus based on an accident scenario of an occupant in a vehicle, the stimulus being a set of proprioceptive signals induced by the accident scenario;

using a neuromuscular model, determining activation and contraction dynamics based on the stimulus, the activation and contraction dynamics representing muscle contraction forces spanning a skeletal system of the occupant;

using a musculoskeletal model, generating, a predicted motor response of the occupant based on the activation and contraction dynamics, the predicted motor response includes a predicted change to postural kinematics of the occupant and a predicted set of driver control actions; and causing a vehicle, based on a predicted outcome given a specified occupant and vehicle model, to initiate active compensation of the vehicle and, in doing so, causing the vehicle to perform an actual physical operation to mitigate a degree of injury to the occupant; and wherein the neuromuscular model uses a Hill-type active state model, where states include r muscle activations, a, and muscle fiber lengths, $l_M$, The state derivatives can be expressed functionally as, $\dot{a}=\dot{a}(a,u)$, and, $\dot{l}_M=\dot{l}_M(q,\dot{q},a,l_M)$, where u is a muscle excitation, and a musculo-tendon force $f_T$ is given as, $f_T=f_T(q,l_M)$, where a relationship between muscle force and joint torque is given by, $\tau=R(q)f_T$, where R is a matrix of muscle moment arms, q is a vector of n generalized or joint coordinates, and τ is a vector of applied joint torques, and when expressed in state space form, musculoskeletal dynamics are, $\dot{v}=M(q)^{-1}[R(q)f_T(q,l_M)-b(q,v)-g(q)-f_{ext}]$, and, $\dot{q}=v$, where M(q), is a joint space mass matrix, $b(q,\dot{q})$, is a vector of centrifugal and Coriolis forces, g(q) is a vector of gravity forces, and $f_{ext}$ are external forces acting on the occupant.

16. The method as set forth in claim 15, further comprising an operation of applying proprioceptive signals from the neuromuscular and musculoskeletal models back to the spinal reflex model.

17. The method as set forth in claim 16, wherein the accident scenario includes one or more parameters indicative of a physical impact to a vehicle having an occupant therein.

18. The method as set forth in claim 17, wherein the spinal reflex model is a functional model of a human spinal cord that models spinal circuits influencing reflexive motor outputs.

19. The method as set forth in claim 18, wherein the active compensation includes adjusting a seat configuration of a seat within the vehicle.

20. The method as set forth in claim 18, further an operation of generating a predicted injury to the occupant based on the accident scenario and the vehicle.

21. The method as set forth in claim 20, further comprising an operation of causing an airline cabin safety design system, based on the predicted injury, to adjust airline cabin design parameters until the predicted injury is below a predetermined threshold.

* * * * *